United States Patent [19]

Beer et al.

[11] Patent Number: 5,021,599

[45] Date of Patent: Jun. 4, 1991

[54] REDOX-RESPONSIVE ANION RECEPTORS

[75] Inventors: Paul D. Beer, Birmingham; Anthony D. Keefe, Surrey, both of United Kingdom

[73] Assignee: Serpentix Conveyor Corporation, Westminster, Colo.

[21] Appl. No.: 401,977

[22] Filed: Aug. 31, 1989

[51] Int. Cl.$^5$ .......................................... C07C 15/12
[52] U.S. Cl. .................................. 556/142; 556/138; 556/143
[58] Field of Search ............... 556/138, 140, 141, 142, 556/143, 144

[56] References Cited

U.S. PATENT DOCUMENTS

| | | | |
|---|---|---|---|
| 2,810,736 | 10/1957 | Catlin et al. | 556/143 X |
| 3,088,961 | 5/1963 | Wilkinson | 556/143 |
| 3,188,335 | 6/1965 | Hubel | 556/142 X |
| 3,417,118 | 12/1968 | Schnettler et al. | 556/143 |
| 3,420,863 | 1/1969 | Schnettler et al. | 556/143 |
| 3,420,865 | 1/1969 | Suh et al. | 556/143 X |
| 3,657,297 | 4/1972 | Spicer et al. | 556/143 |
| 3,673,232 | 6/1972 | Talbot et al. | 556/143 |
| 4,851,598 | 7/1989 | Rosenbaum et al. | 556/138 X |

Primary Examiner—Arthur C. Prescott
Attorney, Agent, or Firm—Kyle W. Rost

[57] ABSTRACT

A family of ligands contains the $(C_5H_4)_2M^+$ moiety as a part of macrocyclic host structure capable of binding an anionic guest, wherein M is a metal ion having at least two valence states, and the host is capable of complexing with a larger fraction of the guest when M is in one of the valence states as compared to the other, for removing the guest anion from solution.

14 Claims, 2 Drawing Sheets

REDOX-RESPONSIVE ANION RECEPTORS

BACKGROUND OF THE INVENTION

1. Field of the Invention

The invention generally relates to organic chemistry and organic compounds. More specifically, the invention relates to heavy metal containing compounds, especially to those containing iron, cobalt, or nickel. The synthesis, electrochemistry, and method of use of polycobalticinium macrocyclic receptor molecules is disclosed.

2. Description of the Prior Art

Anion coordination chemistry, the complexation of anionic species by organic receptor molecules recently has been recognized and developed as a new field of coordination chemistry. Several classes of anion ligands have been reported including Lewis acidic bicyclic tin cryptands, organomercury and silicon macrocycles, quaternary ammonium, polyguanidinium and polyammonium macrocyclic molecules. The latter positively charged pH-dependent class of host form strong and sometimes selective complexes with a variety of anions including the binding of linear dicarboxylates with chain length selectivity.

It would be desirable to produce a class of redox responsive anion receptors that are pH-independent. However, for purposes of regenerating the receptors, pH dependence may be useful.

Similarly, it would be desirable to produce a class of anion receptors that have the ability to bind with selected anions and allow the extraction of such anions from solution.

It would further be desirable to regenerate those receptors and thus have the ability to return some or all to solution to further extract anions.

To achieve the foregoing and other objects and in accordance with the purpose of the present invention, as embodied and broadly described herein, the class of compounds, method of manufacture, and method of use of this invention may comprise the following.

SUMMARY OF THE INVENTION

Against the described background, it is therefore a general object of the invention to provide a family of redox responsive ion receptors to coordinate and respond electrochemically to the binding of ionic guest species.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to the invention, a family of ligands contains the $(C_5H_4)_2M^+$ moiety as a part of a macrocyclic host structure capable of binding an anionic guest, wherein M is a metal ion having at least two valence states, and the host is capable of complexing with a larger fraction of the guest when M is in one of the valence states as compared to the other.

The invention contemplates the method of removing of a selected ion from solution, in which a ligand having the $(C_5H_4)_2M^+$ moiety as a part of a macrocyclic host structure is capable of selectively binding the ion as a guest, wherein M is a metal ion having at least two valence states, and the host is capable of complexing with a larger fraction of the guest when M is in one of the valence states as compared to the other.

The accompanying drawings, which are incorporated in and form a part of the specification illustrate preferred embodiments of the present invention, and together with the description, serve to explain the principles of the invention. In the drawings:

DESCRIPTION OF THE PREFERRED EMBODIMENTS

Figure 1:
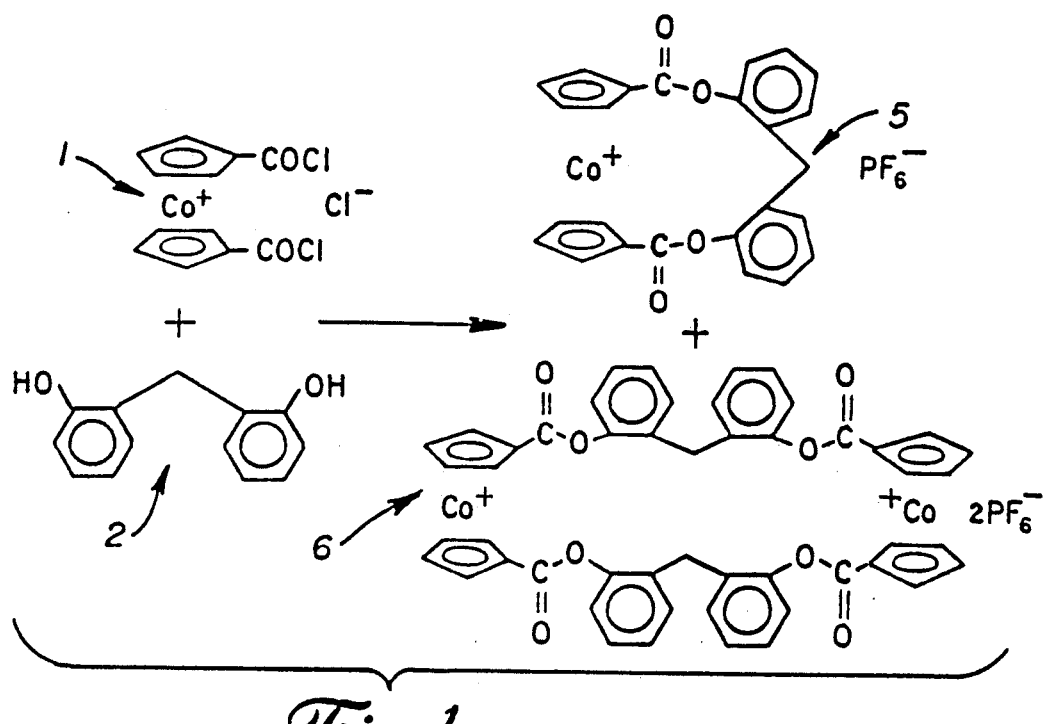
FIG. 1 is a scheme for the synthesis of the hexafluorophosphate salts of compounds (5) and (6).

The invention relates in part to the synthesis and electrochemistry of the first redox responsive class of anion receptor, polycobalticinium macrocycles which are designed to utilize the pH-independent positively charged, eighteen electron air stable, organometallic and redox-active cobalticinium fragment to coordinate and respond electrochemically to the binding of anionic guest species.

This class of receptor has typical structures shown as the anion coordinating units of (5), (6), (7), (8) and (9) shown in the drawings in the form of their $PF_6^-$ salts. One or more macrocycles are bound in combination with a first ion such as a cobalt cation, or other ion, to define a ligand that may be termed the host molecule. The host molecule has the ability to complex with a guest, as by reception of the guest within the cavity of the macrocycle. By this general ability, this class of ligand is capable of extracting the guest from solution and, in some cases, later releasing the guest while the ligand is regenerated and returned to extraction duty.

The structures (5)–(9) are stable in air and in organic solvents such as acetonitrile. The precursor (1) could be condensed with a variety of diols and diamines to produce a variety of macrocyclic products. This family of molecules is characterized by the $(C_5H_5)_2Co^+$ moiety as part of the macrocyclic structure. Cobalt may be replaced by iron or other metal. The neutral ferrocene analogue of ligand (6) has been prepared, and it is anticipated that the ruthenocene and osmocene analogues can be similarly prepared.

A single molecule or moiety of the ligand can include a cation such as cobalt bound within the moiety, and the cation remains capable of further complexing with an anionic guest as shown, for example, at (5). In another form of this class of ligand, the cation binds together two molecules, not necessarily identical molecules, and still is capable of further complexing with an anionic guest, for example, at (6), (7), (8) and (9). In the latter case, because at least one of these cations can be oxidized and reduced to, respectively, higher or lower valence, at least one of those ions is capable of further complexing an anionic guest.

Generally, the cation can be oxidized or reduced to a higher or lower valence. Generally the molecular structure and configuration of the moiety can be arranged so that when the ion is oxidized or at the higher positive valence, the anion or a relatively greater amount of the anion tends to be held as a guest; and when the ion is reduced or at the lower positive valence the anionic guest tends to be released or complexed to a lesser degree.

It is believed that at least some of the host receptors may be selective for one anionic guest form over another anionic guest form. In particular, cobalt has been found to be a powerful cation for use in preparing the host cobalticinium moiety. It is expected that $Mn(3+, 2+)$, $Fe(3+, 2+)$, $Cu(2+, 1+)$, $Ni(3+, 2+)$, $As(5+, 3+)$, and $Sb(3+, 2+)$ analogues will be powerful ligands for removal of anionic species when bound to selected organic molecules. Similarly, it is believed that V, Cr, Ge, Se, Nb, Sn, Hg, Pb and Bi will be similarly useful.

The final physical structure of the molecule, the donor atoms, and donor atom position are each major factors in the control of the selectivity. A cavity or sleeve of the optimum shape, in the optimun size, with the optimun donor atoms in the optimum positions is sought for each potential anionic guest. Thus, the selectivity of any polycobalticinium receptor will ultimately depend upon the topology and charge distribution of the host cavity.

The illustrated ligand moieties (5)-(9) are desired to be selective in their ability to complex and extract by actual anion guest inclusion in the respective polycobalticinium macrocycle. The illustrated $PF_6^-$ salts of (5)-(8) were prepared, in part, because $PF_6^-$ is relatively large and not of favorable geometry to exist inside the host cavities. Thus, the salts are presumed to have vacant cavities, and thus can potentially bind an anion within the cavity. If (5)-(8) were $Cl^-$ salts, it is more likely that at least one $Cl^-$ would be bound inside the respective host's cavity. Thus, in the case of the $PF_6^-$ salts, the $PF_6^-$ is viewed as being a free ion. Ligand moiety (9) is regarded as a model in that infra red and electrochemical evidence suggests that it does not complex anions, but a polymer of (9) may have the ability to bind anions.

The following examples illustrate the syntheses, structural confirmation, and utility of the new ligands.

EXAMPLE 1

Figure 2:
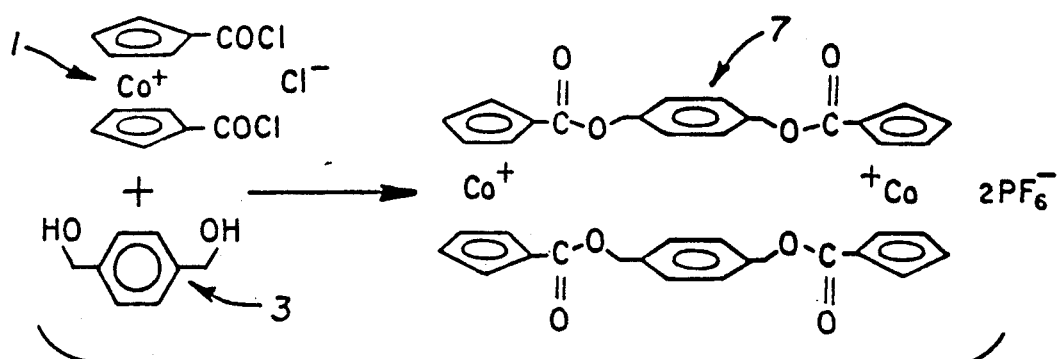
FIG. 2 is a scheme for the synthesis of the hexafluorophosphate salts of compound (7).
Figure 3:
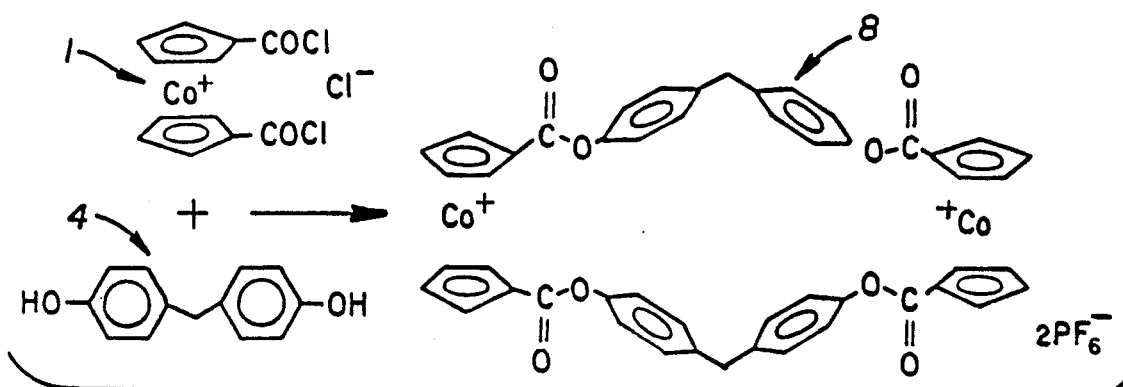
FIG. 3 is a scheme for the synthesis of the hexafluorophosphate salts of compound (8).
Figure 4:
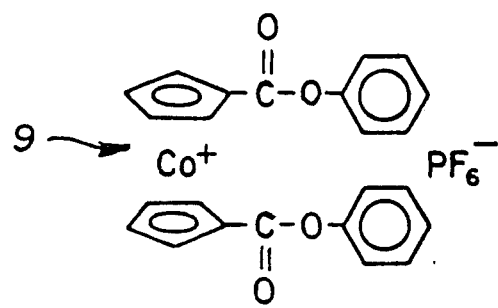
FIG. 4 is the structure of the hexafluorophosphate salts of an acyclic moiety.

With reference to the general method of FIGS. 1-4, the condensation of 1,1'-bis(chlorocarbonyl)cobalticinium chloride (1) with, respectively, 2,2'-bis(hydroxyphenyl)methane (2), 1,4-benzene dimethanol (3) and 4,4'-bis(hydroxyphenyl)methane (4) in the presence of triethylamine followed by column chromatography (Sephadex LH20, acetonitrile) and excess ammonium hexafluorophosphate gave new macrocycles (5), (6), (7) and (8) as yellow powders. Elemental analyses, fast atom bombardment mass spectrometry (FABMS), H n.m.r. and conductivity measurements confirmed the proposed structures.

In detail, the appropriate diol (2 mmol) (Aldrich) and triethylamine (20 mmol) (Aldrich) dissolved in 50/50 toluene and acetonitrile solvent mixture (100 cn³). To this solution was added 1,1'-bis(chlorocarbonyl) cobalticinium chloride (prepared according to J. E. Sheats and M. D. Rausch, J. Org. Chem. 1970, 35, 3254, incorporated by reference herein) (2.4 mmol) in acetonitrile (80 cm³). Resulting reaction mixture stirred at room temperature for 1 hour and solvent removed to give a yellow-green powder. Crude products purified by column chromatography (Sephadex LM20, 95% acetonitrile, 5% water) to give a yellow solid which was recrystallized from acetonitrile in the presence of excess ammonium hexafluorophosphate (13 mmol).

Yields (5) 20%, (6) 60%, (7) 50%, (8) 35%, (9) 60%.

The first evidence indicating that these receptors may complex anionic guests came from FABMS studies. The FABMS spectrum of (8) revealed, in addition to the molecular ion peak at 882, smaller signals at 899, 917 and 1027 mass units tentatively assigned respectively to hydroxide, chloride and hexafluorophosphate complexes. Analogous observations were found with (6) and (7). Fourier transform infra red (FTIR) investigations of the chloride and hexafluorophosphate salts of (6), (7), and (8) revealed up to 8 cm$^{-1}$ differences in the respective carbonyl ester absorption positions. For example, the hexafluorophosphate salt of (6) gave an ester carbonyl stretch at 1747cm$^{-1}$ whereas the analogous chloride salt absorbed at 1739cm$^{-1}$. This effect was not observed with the hexafluorophosphate and chloride salts of the acyclic model (9), suggesting the presence of macrocyclic effect in these systems.

EXAMPLE 2

Anion coordination studies of (6) reveal this receptor to be redox responsive to the binding of the $Br^-$ guest anion, shifting the respective cobalticinium reduction wave to more negative potentials.

Cyclic voltammetric investigations were carried out in acetonitrile using $[n-Bu_4N]BF_4$ as the supporting electrolyte and standard calomel electrode (SCE) as reference. Reversible two electron reduction waves in the region $-0.25$ — $-0.35$ V were observed with (6), (7) and (8). The addition of stoichiometric amounts of tetrabutyl ammonium bromide to electrochemical solutions of (6) led to gradual cathodic shifts of the host's reduction wave. These voltage changes refer to the reversible redox couple

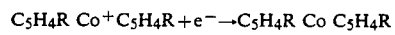

$$C_5H_4R\ Co^+C_5H_4R + e^- \rightarrow C_5H_4R\ Co\ C_5H_4R$$

A maximum shift of 45 mV was observed after four equivalents of bromide salt had been added. The cathodic shift demonstrates that complexation is less when cobalt is in the reduced state.

No cathodic shifts were observed with (9) suggesting bromide anion complexation within the macrocyclic cavity of (6) is essential for electrochemical detection. Analogous experiments with (7), (8) and bromide, with other halide salts were hampered by spontaneous precipitation reactions of the corresponding anion complexed species.

EXAMPLE 3

The receptors (5)-(8) will be immobilized by binding to an insoluble support, silica gel. The supported receptors will be exposed to an aqueous solution of $NO_3^-$ for removal of this anion.

The first portion of the loaded receptors will be regenerated by exposure to acid.

A second portion of the loaded receptors will be regenerated by exposure to NaOH.

The stability of the ester groups will then be determined to select the most suitable regeneration technique.

EXAMPLE 4

The receptors (5)–(8) will be immobilized by binding to a conductive solid support, glassy carbon. The supported receptors will be exposed to an aqueous solution of $NO_3^-$ for removal of this anion.

The loaded receptors will be regenerated by electrochemical reduction of cobalt to cobaltocene, a neutral moiety which will release the anion from being bound.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

The embodiments of the invention in which an exclusive property or privilege is claimed are defined as follows:

1. A family of ligands consisting of at least the $(C_5H_4)_2M^+$ moiety as a part of a macrocyclic host structure, wherein said moiety defines a cavity within the macrocyclic host structure capable of binding an anionic guest, wherein M is a metal ion having at least two valence states, and the host is capable of complexing with a larger fraction of said guest when M is in one of the valence states as compared to the other.

2. The family of claim 1, wherein M is cobalt.

3. The family of claim 1, wherein one member consists of

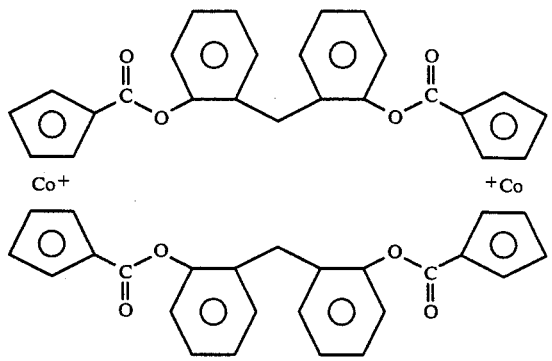

5. The family of claim 1, wherein one member consists of

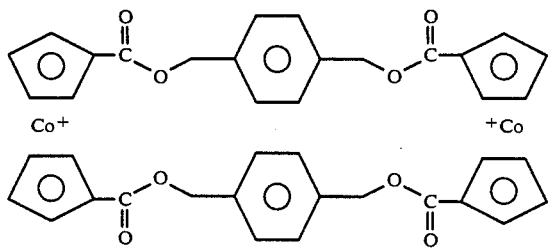

6. The family of claim 1, wherein one member consists of

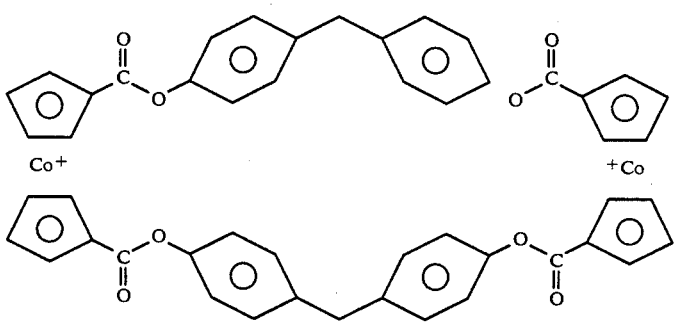

7. The family of claim 1, wherein said moiety comprises $[(C_5H_4)—CO_2—]_2M^+$.

8. The family of claim 1, wherein said moiety comprises $[(C_5H_4)CO_2(C_6H_4)]_2M^+$.

9. A family of ligands comprising the $[(C_5H_4)—CO_2—]_2M^+$ moiety as a part of a host structure capable of binding an anionic quest, wherein M is a metal ion having at least two valence states, and the host is capable of complexing with a larger fraction of said guest when M is in one of the valence states as compared to the other.

10. The family of claim 9, wherein one number consists of

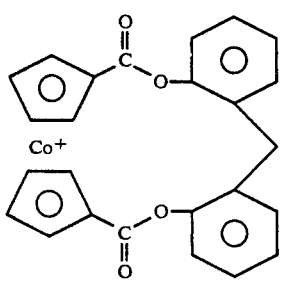

4. The family of claim 1, wherein one member consists of

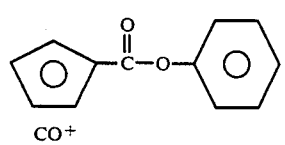

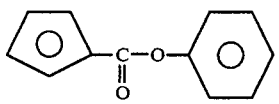

11. The method of removing of a selected ion from solution, comprising adding to the solution a ligand having the $(C_5H_4)_2M^+$ moiety as a part of a macrocyclic host structure capable of selectively binding the ion as a guest, wherein M is a metal ion capable of complexing with a larger fraction of said guest when M is in one of the valence states as compared to the other.

12. The method of claim 11, wherein said moiety comprises $[(C_5H_4)—CO_2—]_2M^+$.

13. The method of claim 11, wherein said moiety comprises $[(C_5H_4)CO_2(C_6H_4)]_2M^+$.

14. A family of ligands consisting of at least:
the $(C_5H_4)_2M^+$ moiety as a part of a macrocyclic host structure, wherein said moiety defines a cavity within the macrocyclic host structure capable of binding an anionic guest, wherein M is a metal ion having at least two valence states, and the host is capable of complexing with a larger fraction of said guest when M is in one of the valence states as compared to the other; and
an anionic guest bound within said cavity.

* * * * *